United States Patent
Holthuizen et al.

(10) Patent No.: US 11,576,729 B2
(45) Date of Patent: Feb. 14, 2023

(54) CRANIAL SURGERY USING OPTICAL SHAPE SENSING

(71) Applicant: KONINKLIJKE PHILIPS N.V., Eindhoven (NL)

(72) Inventors: Ronaldus Frederik Johannes Holthuizen, Odijk (NL); Marco Verstege, Eindhoven (NL); William Edward Peter Van Der Sterren, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 820 days.

(21) Appl. No.: 16/442,642

(22) Filed: Jun. 17, 2019

(65) Prior Publication Data
US 2020/0390502 A1 Dec. 17, 2020

(51) Int. Cl.
*A61B 34/20* (2016.01)
*A61M 27/00* (2006.01)
(Continued)

(52) U.S. Cl.
CPC .......... *A61B 34/20* (2016.02); *A61M 27/006* (2013.01); *A61B 2034/105* (2016.02);
(Continued)

(58) Field of Classification Search
CPC ................. A61M 27/006; A61B 34/20; A61B 2034/105; A61B 2034/2055; A61B 2034/2061; A61B 2090/364
See application file for complete search history.

(56) References Cited

U.S. PATENT DOCUMENTS

| 5,676,673 A | 10/1997 | Ferre |
| 5,800,333 A | 9/1998 | Liprie |

(Continued)

FOREIGN PATENT DOCUMENTS

| WO | 2012/068679 A1 | 5/2012 |
| WO | 2016/038489 A2 | 3/2016 |

OTHER PUBLICATIONS

Mischkowski, Z.M. et al. "Comparison of different registration methods for navigation in craniomaxillofacial surgery" Journal of Crano-Maxillofacial Surgery 36(2):109-16—Mar. 2008.
(Continued)

*Primary Examiner* — Amelie R Davis
*Assistant Examiner* — John Denny Li

(57) ABSTRACT

Various cranial surgery OSS registration device embodiments of the present disclosure encompass a cranial surgery facial mask (128), a mask optical shape sensor (126b) having a mask registration shape extending internally within the cranial surgery facial mask (128) and/or externally traversing the cranial surgery facial mask (128), a cranial surgery tool (101), and a tool optical shape sensor (126d) having a tool registration shape extending internally within the cranial surgery tool (101) and/or externally traversing the cranial surgery tool (101). The mask registration shape of the mask optical shape sensor (126b) and the tool registration shape of the tool optical shape sensor (126d) interactively define a spatial registration of the cranial surgery facial mask (128) and the cranial surgery facial mask (128) and the cranial surgery tool (101) to a cranial image.

15 Claims, 5 Drawing Sheets

(51) Int. Cl.
*A61B 90/00* (2016.01)
*A61B 34/10* (2016.01)

(52) U.S. Cl.
CPC ............... *A61B 2034/2055* (2016.02); *A61B 2034/2061* (2016.02); *A61B 2090/364* (2016.02)

(56) References Cited

U.S. PATENT DOCUMENTS

| | | |
|---|---|---|
| 6,129,670 A | 10/2000 | Burdette et al. |
| 6,428,463 B1 | 8/2002 | Ravins et al. |
| 6,458,068 B1 | 10/2002 | Ellard et al. |
| 7,747,312 B2 | 6/2010 | Barrick |
| 8,206,324 B2 | 6/2012 | Kurono et al. |
| 2002/0087101 A1* | 7/2002 | Barrick ............... A61B 34/20 600/587 |
| 2003/0131852 A1 | 7/2003 | Shafer |
| 2004/0147839 A1* | 7/2004 | Moctezuma de la Barrera .......... A61B 34/20 600/429 |
| 2006/0013523 A1 | 1/2006 | Childlers et al. |
| 2007/0129593 A1 | 6/2007 | Gueye et al. |
| 2010/0215311 A1 | 8/2010 | Moore |
| 2013/0204072 A1 | 8/2013 | Verard et al. |
| 2013/0211261 A1 | 8/2013 | Wang et al. |
| 2020/0069376 A1* | 3/2020 | Garcia ................... A61B 34/20 |

OTHER PUBLICATIONS

International Search Report and Written Opinion dated Aug. 27, 2020 For International Application No. PCT/EP2020/066612 Filed Jun. 16, 2020.

* cited by examiner

CRANIAL SURGERY USING OPTICAL SHAPE SENSING

FIELD OF THE INVENTION

The present disclosure generally relates to cranial surgery (e.g., ventricular drain/shunt placement). The present disclosure specifically relates to utilization of optical shape sensing (OSS) technology to improve cranial surgery, particularly ventricular drain/shunt placement.

BACKGROUND OF THE INVENTION

Ventricular drain/shunt placement from the lateral ventricles of the brain is one of the most common neurological interventions and has high reimbursement. The procedure has historically often been accomplished using a freehand technique, which is not optimal. Often multiple attempts are needed, which results in unnecessary neurological damage. To improve upon the freehand technique, navigated ventricular drain/shunt placements solutions exist that rely on optical navigation, which is often combined with electromagnetic-based navigation.

Specifically, optical navigation is used to register the patient to a pre-op computed tomography (CT) volume via a stereoscopic camera system for optically tracking a pointer or laser scanner measurement of points on the skin of the patient. After registration, a ventricular drain/shunt is placed into cerebrospinal fluid CSF of the patient using the optical navigation for optically tracking a straight rigid drain/shunt placement tool (e.g., a stylet). However, the drain/shunt placement tool typically has a thin diameter (e.g., a metallic inner stylet typically has a 1 millimeter diameter), which frequently results in a bending of the drain/shunt placement tool whereby the optical navigation of the drain/shunt experiences inaccurate tracking of the tool due to a false assumption of a straight rigid drain/shunt placement tool.

Alternatively EM-tracked drain/shunt placement tool may be used to supplement the optical tracking, but a combination of EM tracking and optical tracking has proven to be costly and cumbersome to set up. Further, this EM/optical tracking combination also increases the diameter of the drain/shunt placement tool (e.g., stylet) and is inaccurate when large metallic objects are in the vicinity of the lateral ventricles of the brain, which deters imaging with X-Ray C-arm systems while using EM tracking.

SUMMARY OF THE INVENTION

The present disclosure describes a novel, unique cranial surgery (e.g., ventricular drainage) using optical shape sensing (OSS) technology that is more efficient than cranial surgery using a combination of EM/optical tracking technology.

The present disclosure may be embodied as a cranial surgery OSS registration device, a cranial surgery OSS registration system employing a cranial surgery OSS registration device, and a cranial surgery OSS registration method utilizing a ventricular drain OSS registration device.

Various embodiments of a cranial surgery OSS registration device of the present disclosure encompass a cranial surgery facial mask, a mask optical shape sensor having a mask registration shape extending internally within the cranial surgery facial mask and/or externally traversing the cranial surgery facial mask, a cranial surgery tool, and a tool optical shape sensor having a tool registration shape extending internally within the cranial surgery tool and/or externally traversing the cranial surgery tool.

The mask registration shape of the mask optical shape sensor and the tool registration shape of the tool optical shape sensor interactively define a spatial registration of the cranial surgery facial mask and the cranial surgery tool to a cranial image (e.g., a X-ray/CT image of a cranial anatomical region of a patient or an image of a model of a cranial anatomical region).

The mask optical shape sensor and the tool optical shape sensor may be integrated to constitute a registerable navigation optical shape sensor, or alternatively the mask optical shape sensor and the tool optical shape sensor may be segregated to constitute a registration optical shape sensor and a navigation optical shape sensor, respectively.

As integrated optical shape sensors and as segregated optical shape sensors, the mask registration shape of the mask optical shape sensor and the tool registration shape of the tool optical shape sensor facilitate an automatic spatial registration of the cranial surgery facial mask and the cranial surgery tool to the cranial image.

Further as segregated optical shape sensors, the cranial surgery facial mask may further include fiducials or landmarks whereby the mask registration shape of the mask optical shape sensor and the tool registration shape of the tool optical shape sensor facilitate an automatic spatial registration of the cranial surgery facial mask to the cranial image or a manual spatial registration of the cranial surgery tool to the cranial image involving a contacting of the cranial surgery tool to the fiducials or landmarks.

Various embodiments of a cranial surgery OSS registration system of the present disclosure encompass a cranial surgery OSS registration device of the present disclosure, and an OSS workstation configured to sense the mask registration shape of the mask optical shape sensor and the tool registration shape of the tool optical shape sensor for automatically or manually spatially registering the cranial surgery facial mask and the cranial surgery tool to the cranial image the cranial surgery tool to the cranial image.

Various embodiments of a cranial surgery OSS registration method of the present disclosure encompass a sensing of a mask registration shape of a mask optical shape sensor extending internally within a cranial surgery facial mask and/or externally traversing the cranial surgery facial mask, and a sensing of a tool registration shape of a tool optical shape sensor extending internally within a cranial surgery tool and/or externally traversing the cranial surgery tool.

Various embodiments of a cranial surgery OSS registration method of the present disclosure further encompass a spatial registration (automatic or manual) of the cranial surgery facial mask and the cranial surgery tool to a cranial image based on the sensing of the mask registration shape of the mask optical shape sensor and the sensing of the tool registration shape of the tool optical shape sensor.

For purposes of the description and claims of the present disclosure:

(1) terms of the art including, but not limited to, "cranial surgery", "ventricular drain", "facial mask", "tool", "optical shape sensor", "workstation", "spatial registration", "fiducials", and "anatomical landmarks" are to be interpreted as known in the art of the present disclosure and as exemplary described in the present disclosure;

(2) more particularly, the term "cranial surgery" broadly encompasses any medical procedure related to the cranial region including, but not limited to, ventriculostomy, deep brain stimulation placement, needle placement and neuro catheter based interventions;

(3) more particularly, the term "cranial surgery facial mask" encompasses any facial mask, as known in the art of the present disclosure and hereinafter conceived, covering a preorbital and/or a nasal area of a patient during a cranial surgery;

(4) more particularly, the term "cranial surgery tool" broadly encompasses any tool, as known in the art of the present disclosure and hereinafter conceived, for placing a drain/shunt within lateral ventricles of a brain during a cranial surgery;

(5) the labeling of the term "optical shape sensor" in the present disclosure, such as, for example, as a mask optical shape sensor or a tool optical shape sensor, is for purposes of distinguishing the various optical shape sensors of the present disclosure without limiting or modifying an interpretation of the term "optical shape sensor" as known in the art of the present disclosure and as exemplary described in the present disclosure;

(6) the labeling of the term "workstation" in the present disclosure as OSS workstation is for purposes of specifying a workstation as including functionality for sensing a shape of optical shape sensors without limiting or modifying an interpretation of the term "workstation" as known in the art of the present disclosure and as exemplary described in the present disclosure;

(7) the term "registration shape" broadly encompasses a shape of an optical shape sensor representative of coordinate data applicable for performing a spatial registration as known in the art of the present disclosure and as exemplary described in the present disclosure;

(8) the labeling of the term "registration shape" in the present disclosure, such as, for example, as a mask registration shape or a tool registration shape, is for purposes of distinguishing the various registration shapes of the present disclosure without limiting or modifying an interpretation of the term "registration shape" as known in the art of the present disclosure and as exemplary described in the present disclosure;

(9) more particularly, the term "spatial registration" and various tenses thereof broadly encompasses any registration technique, as known in the art of the present disclosure and hereinafter conceived, for transforming the registration shapes of optical shape sensors into the spatial coordinate system of the cranial image; and

(10) the term "cranial image" broadly encompasses any image illustrative of a cranial anatomical region of a patient or an image of model of a cranial anatomical region.

The foregoing embodiments and other embodiments of the present disclosure as well as various structures and advantages of the present disclosure will become further apparent from the following detailed description of various embodiments of the present disclosure read in conjunction with the accompanying drawings. The detailed description and drawings are merely illustrative of the present disclosure rather than limiting, the scope of the present disclosure being defined by the appended claims and equivalents thereof.

BRIEF DESCRIPTION OF THE DRAWINGS

The present disclosure will present in detail the following description of preferred embodiments with reference to the following figures wherein.

DETAILED DESCRIPTION OF THE PREFERRED EMBODIMENTS

Figure 1A:
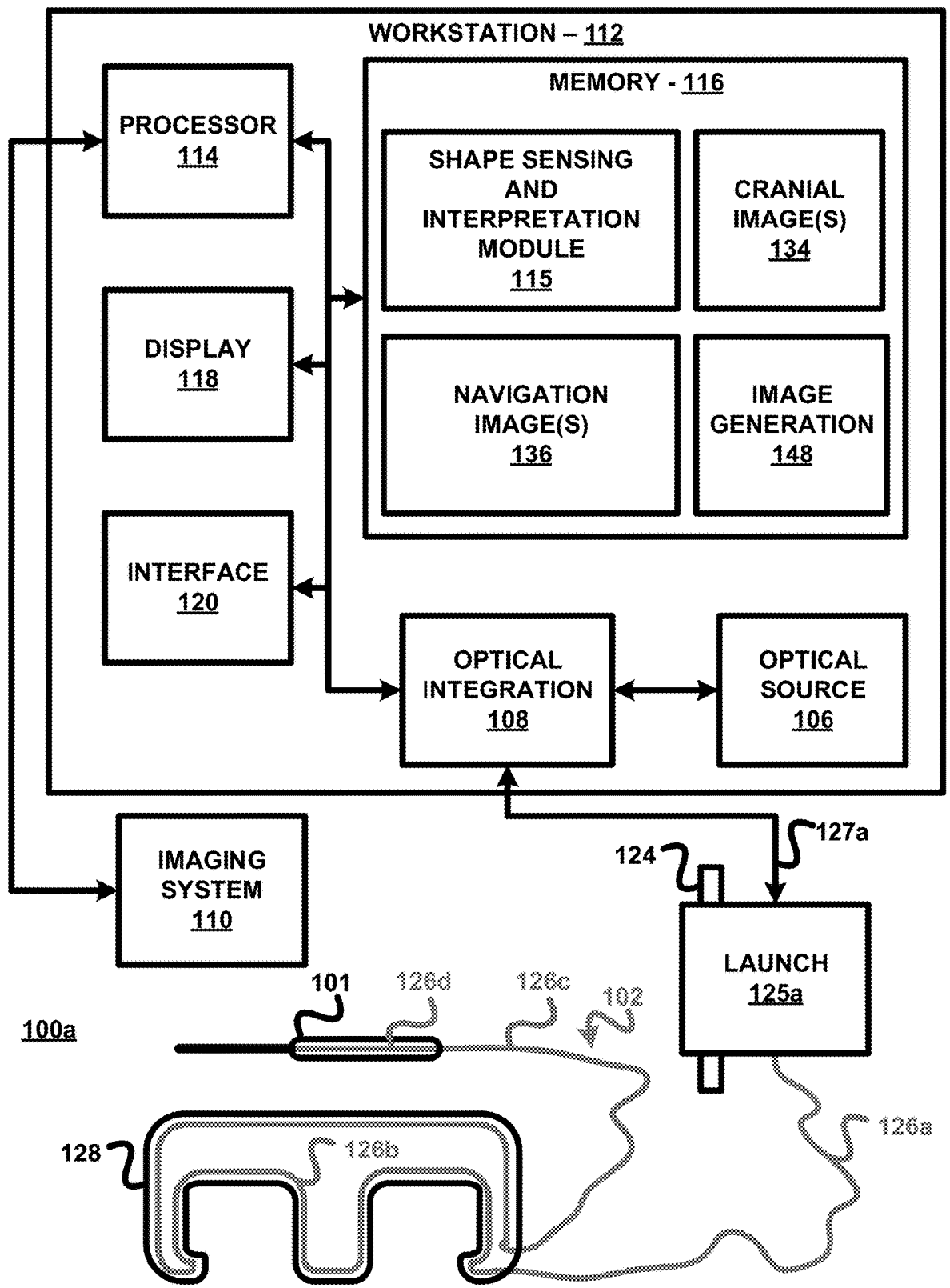
FIG. 1A illustrates a first exemplary embodiment of a ventricular drain OSS registration system employing a first exemplary embodiment of a ventricular drain OSS registration device in accordance with the present disclosure.

The present disclosure is applicable to numerous and various forms of cranial surgical applications as known in the art of the present disclosure and hereinafter conceived including, but not limited to, numerous and various forms of ventriculostomy external ventricular drain via catheters and permanent shunts.

The present disclosure employs optical shape sensing technology in cranial surgical procedures as an improvement over the prior art of a combination of EM-optical tracking of cranial surgery tools, such as, for example, a EM-optical tracking of a placement of drains/shunts within a cerebral ventricle.

More particularly, in accordance with the present principles, devices, systems and methods are provided for optical shape sensing that can be used for spatially registering a cranial surgery tool (e.g., a ventricular drain stylet). In one embodiment of the present disclosure, the optical shape sensing employs shape sensing optical fiber(s) incorporated within cranial surgery facial masks and cranial surgery tools of the present disclosure, and the shape sensing measurement can be registered to a cranial image. The registered position of the cranial surgery tools with respect to the cranial image may be displayed for a user.

In practice, optical shape sensing uses light along a multicore optical fiber to reconstruct the shape along that fiber. The principle involved makes use of distributed strain measurement in the optical fiber using characteristic Rayleigh backscatter or controlled grating patterns. The shape along the optical fiber begins at a specific point along the sensor, known as the launch or z=0, and the subsequent shape position and orientation are relative to that point. The optical fiber may be, e.g., 200 microns in diameter, and may be up to a few meters long while maintaining millimeter-level accuracy. Optical shape sensing fibers may be incorporated into a wide range of medical devices to provide live guidance medical procedures. As an example, a ventricular drain tool (e.g., a stylet, such as a stylet for placements of shunts or ventricular catheters) may be employed for a placement of drains/shunts within a cerebral ventricle with the optical shape sensing measurement overlaid upon a pre-operative or intra-operative cranial image. The position/orientation measured by the optical shape sensing is used to update the navigation visualization on a display.

An example of optical shape sensing navigation for cranial surgical applications employs relative positions of a cranial surgery facial masks and a cranial surgery tools to a patient face, which are each sensed with an optical shape sensor incorporated therein. The optical shape sensors are co-registered to each other, e.g., at a launch position. The optical reflection or scatter returns back to a console that outputs the position of cranial surgery tool within the coordinate system of the cranial image, which can be displayed to the operator.

It should be understood that a workstation and imaging system depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Figure 1B:
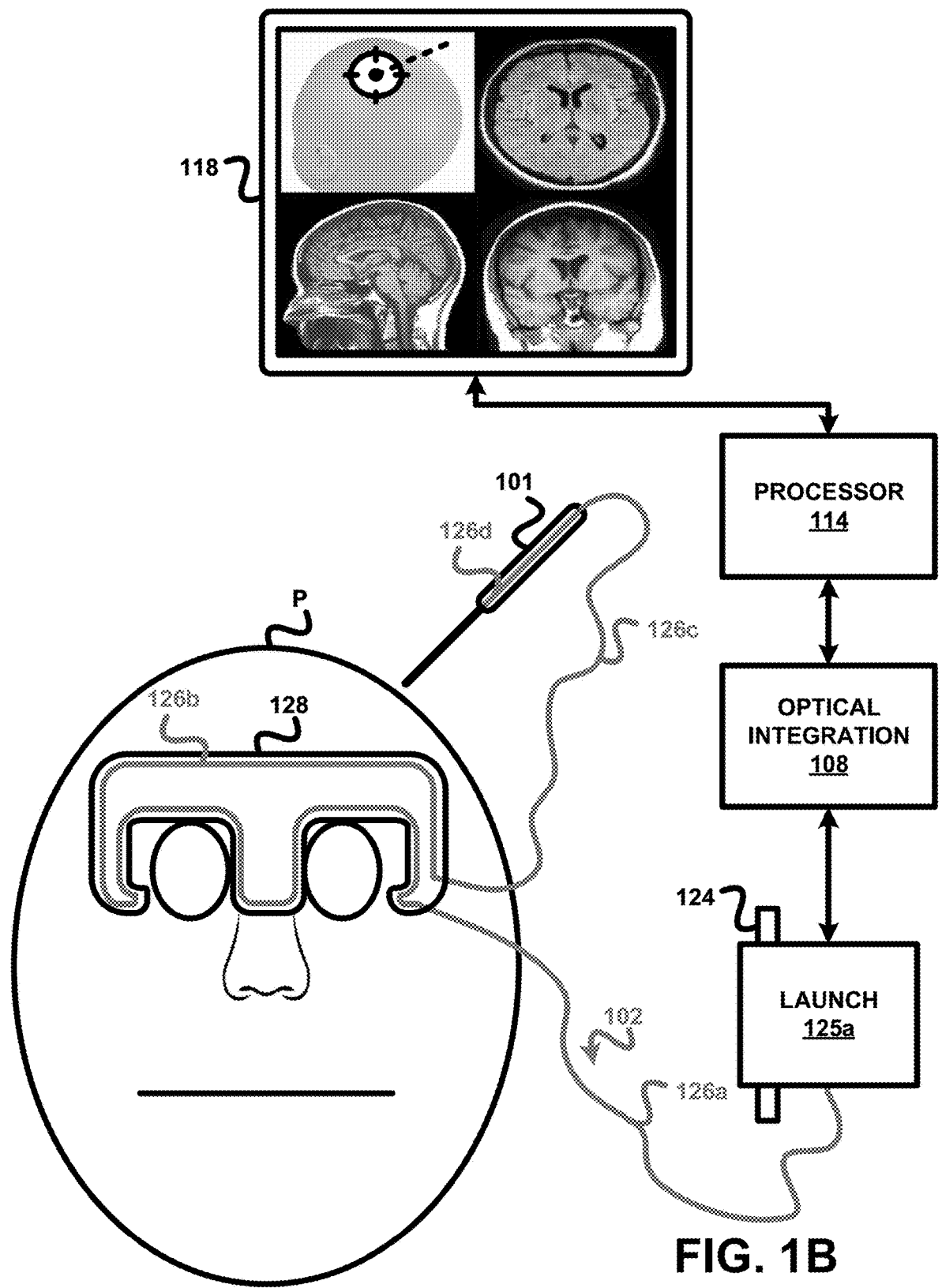
FIG. 1B illustrates an exemplary operation of the ventricular drain OSS registration system of FIG. 1A in accordance with the present disclosure.

To facilitate an understanding of the present disclosure, the following description of FIGS. 1A and 1B teaches an exemplary embodiments of a ventricular drain OSS registration system employing a ventricular drain OSS registration device having a registrable navigation optical shape sensor in accordance with the present disclosure. While FIGS. 1A and 1B will be described in the context of a ventriculostomy, those having ordinary skill in the art of the present disclosure will appreciate how to apply the present disclosure to make and use additional embodiments of a cranial surgical OSS registration system employing a cranial surgical OSS registration device having a registrable navigation optical shape sensor in accordance with the present disclosure for a variety of cranial surgical procedures.

Referring to FIG. 1A, a ventricular drain OSS registration system 100a of the present disclosure implements numerous and various forms of ventriculostomy utilizing a shape sensing enabled ventricular drain facial mask 128 and a shape sensing enabled ventricular drain tool 101 as illustratively shown. Ventricular drain OSS registration system 100a may include a workstation or console 112 from which a procedure is supervised and/or managed. Workstation 112 preferably includes one or more processors 114 and memory 116 for storing programs and applications. Memory 116 may store a shape sensing and interpretation module 115 configured to interpret optical feedback signals from a shape sensor 102. Interpretation module 115 is configured to use the optical fiber signal feedback to reconstruct a shape of a registerable navigation optical shape sensor 102. The interpretation module 115 is configured to provide information for a real-time visualization of the position and orientation of shape sensing enabled ventricular drain tool 101 within one or more cranial images 134.

The optical shape sensing technology is embodied as a registrable navigation optical shape sensor 102 composed on a single set of optical fibers defining a sequential integration of (1) a launch optical shape sensor 126a having a proximal end connected to a launch 125a, (2) a mask optical shape sensor 126b extending internally within and/or externally traversing a shape sensing enabled ventricular drain facial mask 128, (3) a positioning optical shape sensor 126c, and (4) a tool optical shape sensor 126d extending internally within or externally traversing a shape sensing enabled ventricular drain tool 101 (e.g., a stylet). Each optical shape sensor 126a-126d includes optical fibers which are configured in a set pattern or patterns. The optical fibers connect to the workstation 112 through launch mount 125a and cabling 127a (including a communication optical fiber). The cabling 127a may include fiber optics, electrical connections, other instrumentation, etc., as needed. The cabling 127a interfaces with an optical interrogation unit 108 that may include or work with an optical source 106. The optical interrogation unit 108 sends and receives optical signals from registrable navigation optical shape sensor 102. An operating room rail 124 or other reference position may include the launch mount 125a that includes a reference point or launch point (z=0) for the one or more optical fiber sensors.

In practice, optical shape sensor 126a-126d with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric minor. A fiber Bragg grating can therefore be used as an inline optical filter to block certain wavelengths, or as a wavelength-specific reflector.

Also in practice, optical shape sensors 126a-126d with fiber optics may be based on inherent backscatter. One such approach uses Rayleigh scatter (or other scattering) in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multi-core fiber, the 3D shape and dynamics of the surface of interest can be followed.

Fiber Bragg Gratings (FBGs) may also be employed for OSS, which use Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optic sensors. In an FBG sensor, the measurand (e.g., strain) causes a shift in the Bragg wavelength.

One advantage of OSS is that various sensor elements can be distributed over the length of a fiber. Incorporating three or more cores with various sensors (gauges) along the length of a fiber that is embedded in a structure permits a three-dimensional form of such a structure to be precisely determined, typically with better than 1 mm accuracy. Along the length of the fiber, at various positions, a multitude of FBG sensors can be located. From the strain measurement of each FBG, the curvature of the structure can be inferred at that position. From the multitude of measured positions, the total three-dimensional form is determined.

Workstation 112 further includes an image generation module 148 configured to receive feedback from the registrable navigation optical shape sensor 102 and record position data as to where the one or more optical shape sensors 126a-126d relative to a cranial anatomical region of patient as will further described with the subsequent description of FIG. 1B of the present disclosure.

Workstation 112 further includes a display 118 for viewing cranial image(s) 134 collected by an imaging system 110 (e.g., CT, ultrasound, fluoroscopy, MRI, etc.). Display 118 may also permit a user to interact with the workstation 112 and its components and functions, or any other element within the ventricular drain OSS registration system 100a. This is further facilitated by an interface 120 which may include a keyboard, a mouse, a joystick, a haptic device, or any other peripheral or control to permit user feedback from and interaction with the workstation 112.

The ventricular drain OSS registration system 100a is based on optical fiber shape sensing and can be used for displaying the relative position and orientation of shape sensing enabled ventricular drain tool 101 (e.g., a stylet) to cranial anatomical region of a patient.

More particularly, referring to FIG. 1B, launch optical shape sensor 126a facilitates a registration placement of shape sensing enabled ventricular drain facial mask 128 over the relevant anatomical information of a patient P during a ventriculostomy (e.g., a periorbital and a nasal area) whereby mask optical shape sensor 126b has a registration shape to automatically register and track the shape sensing enabled ventricular drain facial mask 128 to the cranial image dataset shown on display 118 (e.g., a pre-op CT dataset), which registers and tracks the patient P to the cranial image dataset. Positioning optical shape sensor 126c facilitates a positioning of shape sensing enabled ventricular drain tool 101 relative to the cranial anatomical region of the patient P wherein tool optical shape sensor 126d has a registration shape to automatically register and track a position and a curvature of the shape sensing enabled ventricular drain tool 101 to the cranial image dataset shown on display 118.

Via launch 125a, optical interrogation unit 108 sends and receives optical signals from optical shape sensors 126a-126d whereby processor 114 calculates a 3D position of the optical shape sensors 126a-126d and performs the registration and tracking of the shape sensing enabled ventricular drain facial mask 128 and shape sensing enabled ventricular drain tool 101 to the cranial image dataset. As the ventriculostomy is being performed, display 118 will show the location and orientation of the shape sensing enabled ventricular drain tool 101 in relationship to the cranial image dataset, or derived information thereof such as a planned trajectory or segmentation of the ventricles.

Figure 2A:
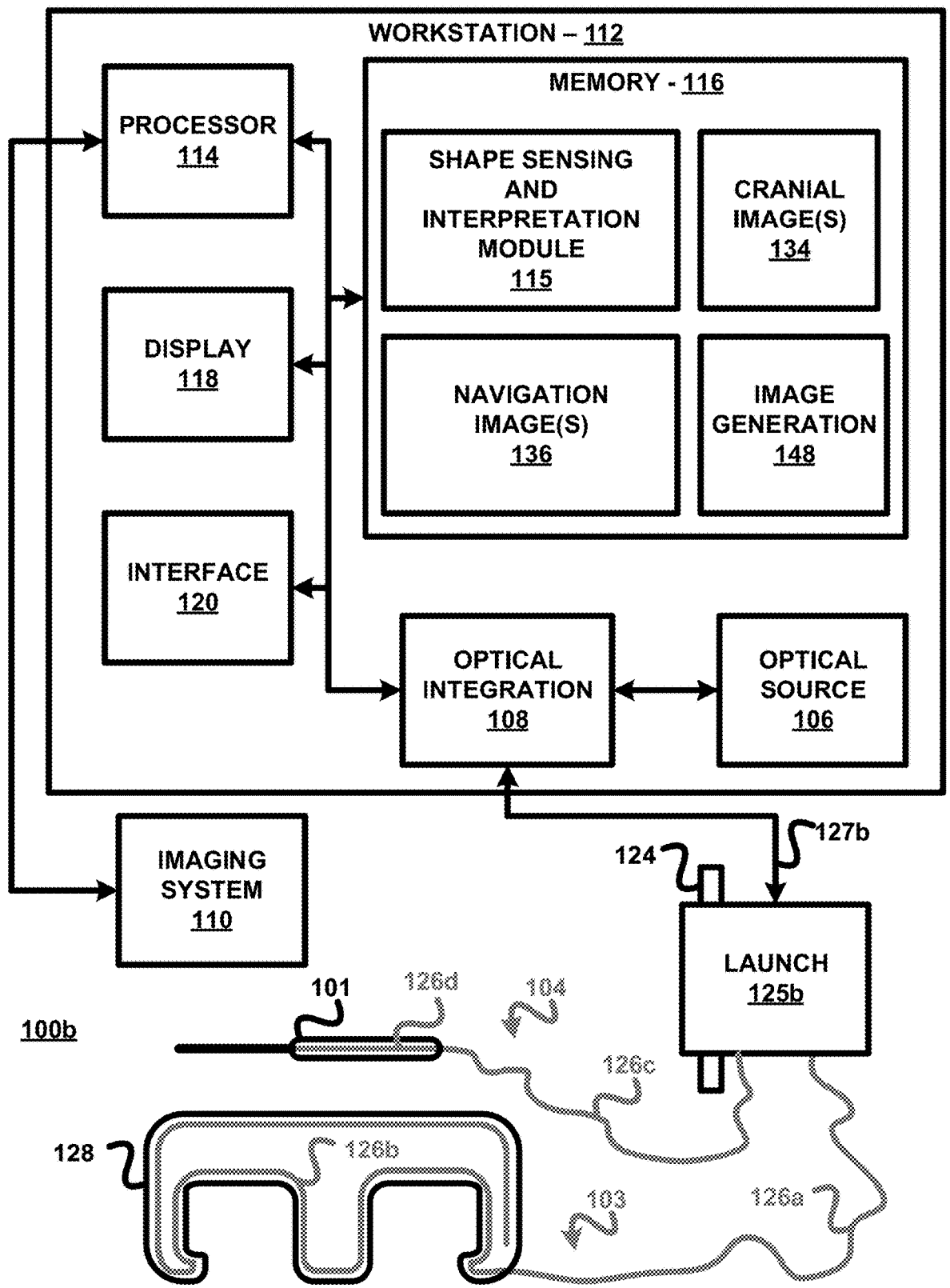
FIG. 2A illustrates a second exemplary embodiment of a ventricular drain OSS registration system employing a second exemplary embodiment of a ventricular drain OSS registration device in accordance with the present disclosure.
Figure 2B:
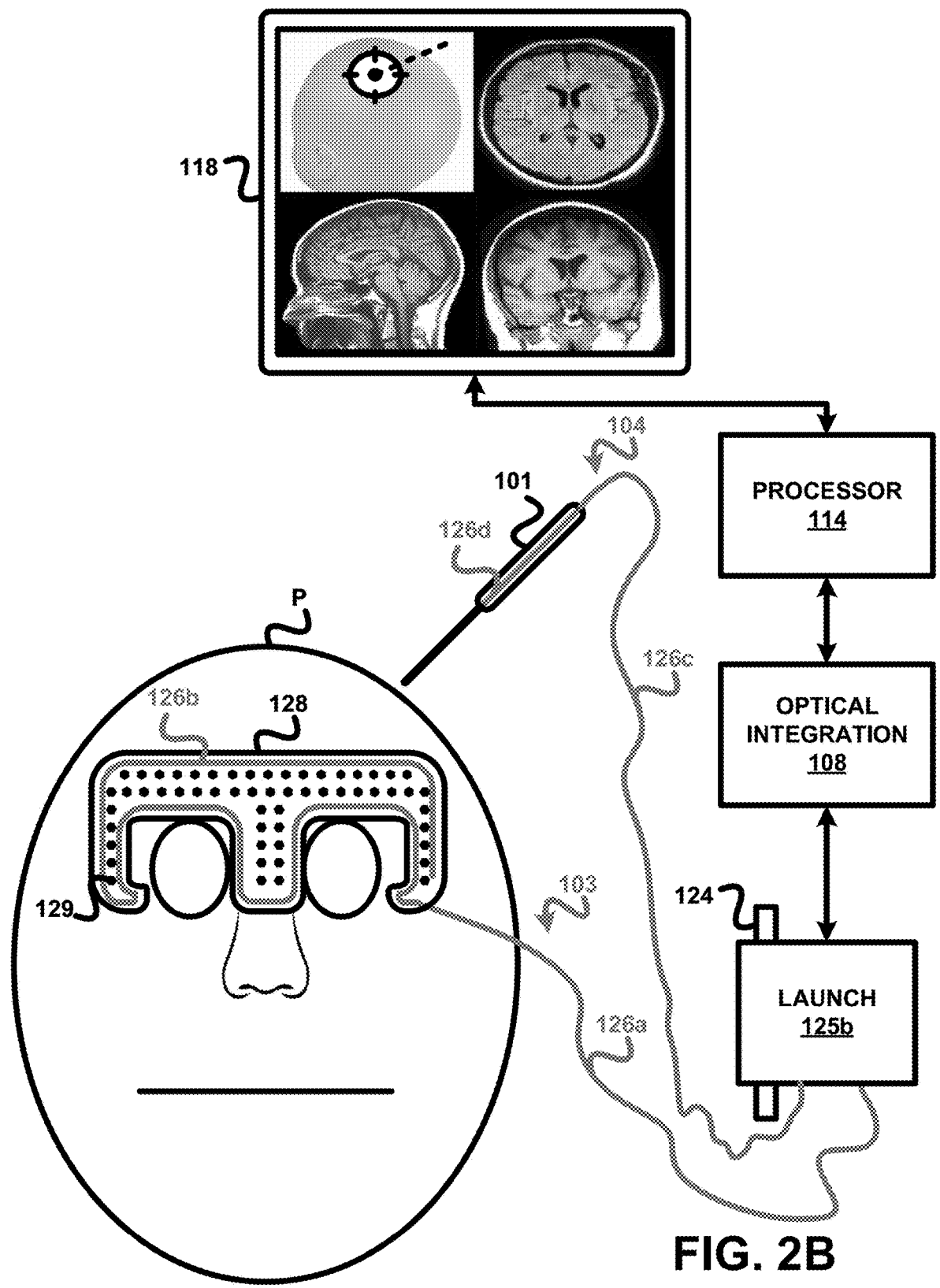
FIG. 2B illustrates an exemplary operation of the ventricular drain OSS registration system of FIG. 2A in accordance with the present disclosure.

To facilitate a further understanding of the present disclosure, the following description of FIGS. 2A and 2B teaches an exemplary embodiments of a ventricular drain OSS registration system employing a ventricular drain OSS registration device having a registration optical shape sensor and a navigation optical shape sensor in accordance with the present disclosure. From the description of FIGS. 2A and 2B, those having ordinary skill in the art of the present disclosure will appreciate how to apply the present disclosure to make and use additional embodiments of a ventricular drain OSS registration system employing a ventricular drain OSS registration device having a registration optical shape sensor and a navigation optical shape sensor in accordance with the present disclosure.

Referring to FIG. 2A, similar to ventricular drain OSS registration system 100a of FIG. 1A, a ventricular drain OSS registration system 100b of the present disclosure implements numerous and various forms of ventriculostomy utilizing a shape sensing enabled ventricular drain facial mask 128 and a shape sensing enabled ventricular drain tool 101 as illustratively shown.

Ventricular drain OSS registration system 100b includes workstation 112 and imaging system 110 as previously described in connection with FIG. 1A of the present disclosure.

Alternative to ventricular drain OSS registration system 100a, the optical shape sensing technology is embodied as a registration optical shape sensor 103 composed of one set of optical fibers defining a sequential integration of (1) the launch optical shape sensor 126a having a proximal end connected to a launch 125b and (2) the mask optical shape sensor 126b extending internally within and/or externally traversing shape sensing enabled ventricular drain facial mask 128. The optical shape sensing technology is further embodied as a navigation optical shape sensor 104 composed of another set of optical fibers defining a sequential integration (1) the positioning optical shape sensor 126c having a proximal end connected to a launch 125b, and (2) the tool optical shape sensor 126d extending internally within or externally traversing a shape sensing enabled ventricular drain tool 101 (e.g., a stylet). Again, each optical shape sensor 126a-126d includes optical fibers which are configured in a set pattern or patterns. The optical fibers connect to the workstation 112 through launch mount 125b and cabling 127b (including a communication optical fiber). The cabling 127b may include fiber optics, electrical connections, other instrumentation, etc., as needed. The cabling 127b interfaces with an optical interrogation unit 108 that may include or work with an optical source 106. The optical interrogation unit 108 sends and receives optical signals to/from registration optical shape sensor 103 and navigation optical shape sensor 104. An operating room rail 124 or other reference position may include the launch mount 125b that includes one reference point or launch point (z=0) for registration optical shape sensor 103 and another reference point or launch point (z=0) for navigation optical shape sensor 104.

ventricular drain OSS registration system 100a (FIG. 1A), the ventricular drain OSS registration system 100b is based on optical fiber shape sensing and can be used for displaying the relative position and orientation of shape sensing enabled ventricular drain tool 101 (e.g., a stylet) to a cranial anatomical region of a patient.

More particularly, referring to FIG. 2B, launch optical shape sensor 126a facilitates a registration placement of shape sensing enabled ventricular drain facial mask 128 over the relevant anatomical information of a patient P during a ventriculostomy (e.g., a periorbital and a nasal area) whereby mask optical shape sensor 126b has a registration shape to register and track shape sensing enabled ventricular drain facial mask 128 to the cranial image dataset shown on display 118 (e.g., a pre-op CT dataset), which is results in patient P being registered and tracked to the cranial image dataset. Positioning optical shape sensor 126c facilitates a positioning of shape sensing enabled ventricular drain tool 101 relative to the cranial anatomical region of the patient P wherein tool optical shape sensor 126d has a registration shape to register and track a position and a curvature of the shape sensing enabled ventricular drain tool 101 to the cranial image dataset shown on display 118.

In practice, if the spatial relationship of the launch points is known, then shape sensing enabled ventricular drain facial mask 128 and shape sensing enabled ventricular drain tool 101 are automically registered and tracked to the cranial image dataset.

shape sensing enabled ventricular drain facial mask 128 may include imagable fiducials/landmarks 129 to facilitate a manual registration of patient P and shape sensing enabled ventricular drain tool 101 to the cranial image dataset via a contacting of the shape sensing enabled ventricular drain tool 101 to the fiducials/landmarks 129 as known in the art of thre present disclosure.

Via launch 125b, optical interrogation unit 108 sends and receives optical signals to/from optical shape sensors 126a-126d whereby processor 114 calculates a 3D position of the optical shape sensors 126a-126d and performs the registration and tracking of the shape sensing enabled ventricular drain facial mask 128 and shape sensing enabled ventricular drain tool 101 to the cranial image dataset. Again, as the ventriculostomy is being performed, display 118 will show the location and orientation of the shape sensing enabled ventricular drain tool 101 in relationship to the cranial image dataset, or derived information thereof such as a planned trajectory or segmentation of the ventricles.

Figure 3:
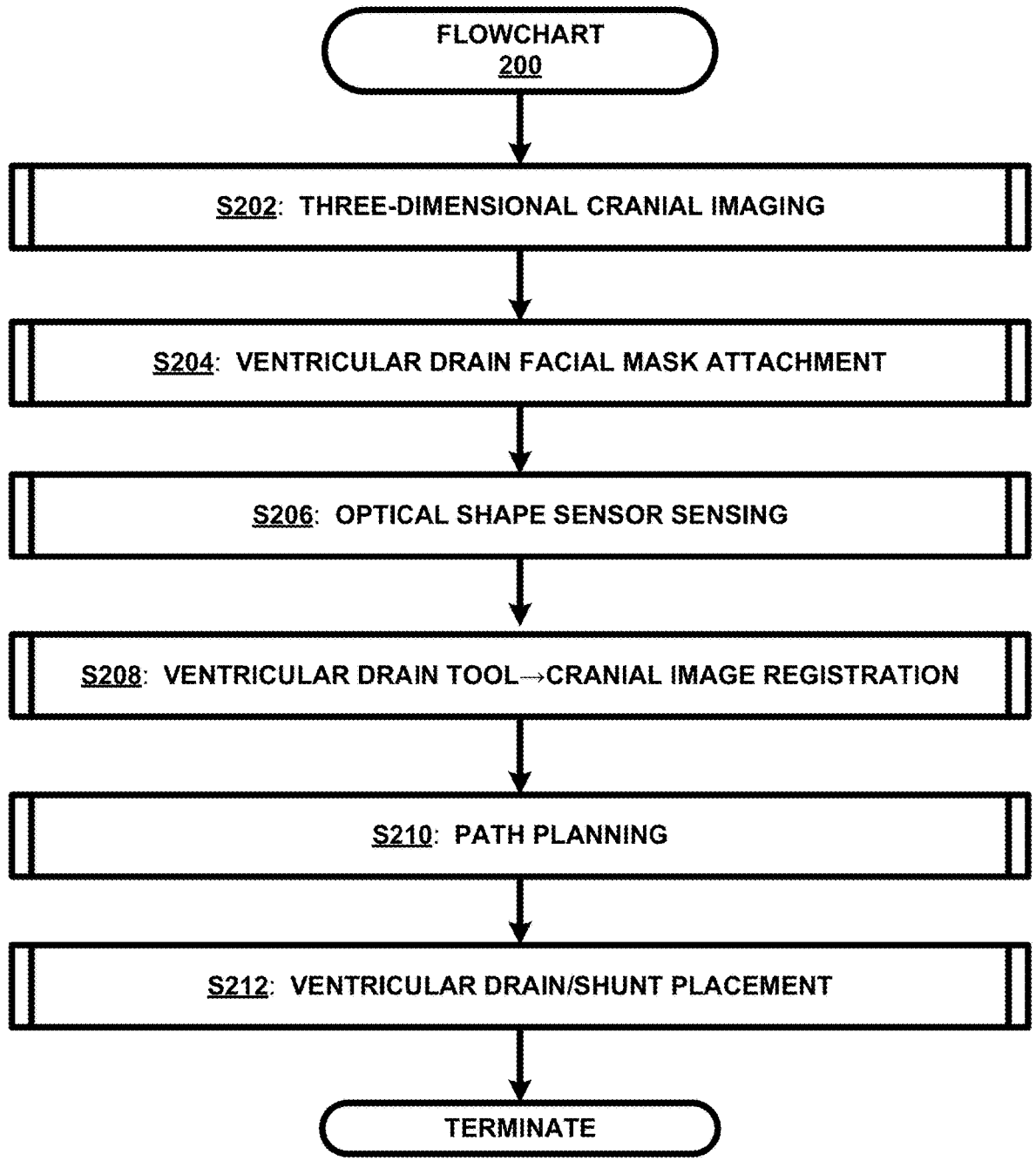
FIG. 3 illustrates a flowchart representative of an exemplary embodiment of a ventricular drain OSS registration method involving a ventricular drain OSS registration device in accordance with the present disclosure.

To facilitate a further understanding of the present disclosure, the following description of FIG. 3 teaches an exemplary embodiments of a ventricular drain OSS registration method utilizing a ventricular drain OSS registration device in accordance with the present disclosure. From the description of FIG. 3, those having ordinary skill in the art of the present disclosure will appreciate how to apply the present disclosure to make and use additional embodiments of a ventricular drain OSS registration methods utilizing a ventricular drain OSS registration device in accordance with the present disclosure.

Referring to FIG. 3, prior to or during a ventriculostomy, a stage S202 of a flowchart 200 encompasses imaging system 110 (FIGS. 1 and 2) being operated to generate a pre-op or intra-op 3D cranial image. During the ventriculostomy, a stage S204 of flowchart 200 encompasses a placement of a shape sensing enabled ventricular drain facial mask 128 onto a patient, a stage S206 of flowchart 200 encompasses optical interrogation unit 108 (FIGS. 1 and 2) and optical source 106 (FIGS. 1 and 2) for a sensing of optical shape sensors 126, and a stage S208 of flowchart 200 encompasses processor 114 (FIGS. 1 and 2) processing optical sensing signals via interpretation module 115 to implement the registration of shape sensing enabled ventricular drain facial mask 128 and shape sensing enabled ventricular drain tool 101 to the cranial image dataset.

Still referring to FIG. 3, a stage S210 of flowchart 200 encompasses processor path planning within the cranial image dataset as known in the present disclosure, and a stage S212 of flowchart 200 encompasses processor 114 (FIGS. 1 and 2) processing optical sensing signals via interpretation module 115 to implement the tracking of shape sensing enabled ventricular drain facial mask 128 and shape sensing enabled ventricular drain tool 101 to the cranial image dataset as the ventricular drain/shunt is placed within the patient P in accordance with the planned path.

Still referring to FIG. 3, fiducials/landmarks may be utilized during flowchart 200 to facilitate the registration between the shape sensing enabled ventricular drain facial mask 128/shape sensing enabled ventricular drain tool 101 to cranial images.

In one exemplary embodiment, an arrangement of fiducials in/on the shape sensing enabled ventricular drain facial mask 128 match a shape of the shape sensing enabled ventricular drain facial mask 128, and the fiducials are radiopaque (or MR compatible or so) whereby the fiducials are easy to find in a pre-operative scan to thereby facilitate registration during stage S208 of the shape sensing enabled ventricular drain facial mask 128/shape sensing enabled ventricular drain tool 101 to the pre-operative scan. Alternatively, the registration may be done automatically without the use of fiducials, because of the uniqueness of the shape of the head known from the pre-operative scan and OSS in the shape sensing enabled ventricular drain facial mask 128.

In a second exemplary embodiment, landmarks in/on the shape sensing enabled ventricular drain facial mask 128 facilitate a manual registration between shape sensing enabled ventricular drain facial mask 128 and shape sensing enabled ventricular drain tool 101 when needed, such as, for example, when the spatial positional relationship between the OSS sensor of shape sensing enabled ventricular drain facial mask 128 and the OSS sensor of shape sensing enabled ventricular drain tool 101 is unknown (i.e., the OSS sensors are attached to different launch bases).

In a third exemplary embodiment, landmarks on the shape sensing enabled ventricular drain facial mask 128 are manually used to position shape sensing enabled ventricular drain facial mask 128 correctly on the face of the patient P, particularly via placement instructions/guidance.

Referring to FIGS. 1-3, those of ordinary skill in the art of the present disclosure will appreciate the numerous advantages and benefits of the present disclosure including, but not limited to, an efficient navigation of cranial surgical tools during a cranial surgical procedure, such as, for example, an efficient navigation of a stylet during a ventriculostomy.

In interpreting the appended claims, it should be understood that: (a) the word "comprising" does not exclude the presence of other elements or acts than those listed in a given claim; (b) the word "a" or "an" preceding an element does not exclude the presence of a plurality of such elements; (c) any reference signs in the claims do not limit their scope; and (d) no specific sequence of acts is intended to be required unless specifically indicated.

Having described preferred embodiments for shape sensing for orthopedic navigation (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A cranial surgery optical shape sensing (OSS) registration device, comprising:
    a cranial surgery facial mask;
    a mask optical shape sensor having a mask registration shape at least one of extending internally within the cranial surgery facial mask and externally traversing the cranial surgery facial mask;
    a cranial surgery tool;
    a tool optical shape sensor having a tool registration shape at least one of extending internally within the cranial surgery tool or externally traversing the cranial surgery tool; and
    wherein: the mask registration shape of the mask optical shape sensor and the tool registration shape of the tool optical shape sensor interactively define a spatial registration of the cranial surgery facial mask and the cranial surgery tool to a cranial image; wherein the mask optical shape sensor and the tool optical shape sensor are sequentially integrated.

2. The cranial surgery OSS registration device of claim 1, wherein the mask optical shape sensor and the tool optical shape sensor are integrated to constitute a registerable navigation optical shape sensor.

3. The cranial surgery OSS registration device of claim 1, wherein the mask optical shape sensor and the tool optical shape sensor are segregated to constitute a registration optical shape sensor and a navigation optical shape sensor.

4. The cranial surgery OSS registration device of claim 1, wherein the cranial surgery facial mask further incorporates fiducials.

5. The cranial surgery OSS registration device of claim 1, wherein the cranial surgery facial mask further incorporates landmarks.

6. A cranial surgery optical shape sensing (OSS) registration system, comprising:
    a cranial surgery facial mask;
    a mask optical shape sensor having a mask registration shape at least one of extending internally within the cranial surgery facial mask and externally traversing the cranial surgery facial mask;
    a cranial surgery tool;
    a tool optical shape sensor having a tool registration shape at least one of extending internally within the cranial surgery tool or externally traversing the cranial surgery tool;
    wherein: the mask registration shape of the mask optical shape sensor and the tool registration shape of the tool optical shape sensor interactively define a spatial registration of the cranial surgery facial mask and the cranial surgery tool to a cranial image; and the mask optical shape sensor and the tool optical shape sensor are sequentially integrated; and
    an OSS workstation configured to sense the mask registration shape of the mask optical shape sensor and the tool registration shape of the tool optical shape sensor for spatially registering of the cranial surgery facial mask and the cranial surgery tool to the cranial image.

7. The cranial surgery OSS registration system of claim 6, wherein the mask optical shape sensor and the tool optical shape sensor are integrated to constitute a registerable navigation optical shape sensor.

8. The cranial surgery OSS registration system of claim 6, wherein the mask optical shape sensor and the tool optical shape sensor are segregated to constitute a registration optical shape sensor and a navigation optical shape sensor.

9. The cranial surgery OSS registration system of claim 6, wherein the cranial surgery facial mask further incorporates fiducials.

10. The cranial surgery OSS registration system of claim 6, wherein the cranial surgery facial mask further incorporates landmarks.

11. A cranial surgery optical shape sensing (OSS) registration method, comprising:
    sensing a mask registration shape of a mask optical shape sensor at least one of extending internally within a cranial surgery facial mask and externally traversing the cranial surgery facial mask;
    sensing a tool registration shape of a tool optical shape sensor at least one of extending internally within a cranial surgery tool or externally traversing the cranial surgery tool; and
    spatially registering of the cranial surgery facial mask and the cranial surgery tool to a cranial image based on the sensing of the mask registration shape of the mask optical shape sensor and the sensing of the tool registration shape of the tool optical shape sensor, wherein the mask optical shape sensor and the tool optical shape sensor are sequentially integrated.

12. The cranial surgery OSS registration method of claim 11, wherein the mask optical shape sensor and the tool optical shape sensor are integrated to constitute a registerable navigation optical shape sensor.

13. The cranial surgery OSS registration method of claim 12, wherein spatial registering of the cranial surgery tool to a cranial image is an automatic spatial registration derived from the sensing of the mask registration shape of the mask optical shape sensor and the sensing of the tool registration shape of the tool optical shape sensor.

14. The cranial surgery OSS registration method of claim 11, wherein the mask optical shape sensor and the tool optical shape sensor are segregated to constitute a registration optical shape sensor and a navigation optical shape sensor.

15. The cranial surgery OSS registration method of claim 14, wherein the cranial surgery facial mask includes at least one of fiducials and landmarks; and wherein the spatial registering of the cranial surgery tool to a cranial image is a manual spatial registration including contacting the cranial surgery tool to at least one of the fiducials and the landmarks.

* * * * *